(12) United States Patent
Wong et al.

(10) Patent No.: US 9,944,627 B2
(45) Date of Patent: Apr. 17, 2018

(54) SPIROACRIDINE-TRIAZINE HYBRIDS AND APPLICATIONS FOR ELECTROLUMINESCENT DEVICES

(71) Applicant: National Taiwan University, Taipei (TW)

(72) Inventors: Ken-Tsung Wong, Taipei (TW); Chung-Chih Wu, Taipei (TW); Tanmay Chatterjee, Taipei (TW); Ting-An Lin, Taipei (TW); Wei-Lung Tsai, Taipei (TW); Meng-Jung Wu, Taipei (TW)

(73) Assignee: NATIONAL TAIWAN UNIVERSITY, Taipei (TW)

( * ) Notice: Subject to any disclaimer, the term of this patent is extended or adjusted under 35 U.S.C. 154(b) by 0 days.

(21) Appl. No.: 15/590,394

(22) Filed: May 9, 2017

(65) Prior Publication Data
US 2017/0320855 A1    Nov. 9, 2017

Related U.S. Application Data

(60) Provisional application No. 62/391,663, filed on May 9, 2016.

(51) Int. Cl.
| | |
|---|---|
| *C07D 403/02* | (2006.01) |
| *C09K 11/07* | (2006.01) |
| *C07D 487/10* | (2006.01) |
| *C07D 255/02* | (2006.01) |
| *C07D 221/06* | (2006.01) |
| *C07D 221/22* | (2006.01) |
| *C07D 253/065* | (2006.01) |
| *H01L 51/00* | (2006.01) |
| *C07D 403/12* | (2006.01) |
| *C07D 403/06* | (2006.01) |
| *C07D 403/08* | (2006.01) |
| *C07D 403/10* | (2006.01) |

(52) U.S. Cl.
CPC ......... *C07D 403/02* (2013.01); *C07D 221/06* (2013.01); *C07D 221/22* (2013.01); *C07D 253/065* (2013.01); *C07D 255/02* (2013.01); *C07D 403/06* (2013.01); *C07D 403/08* (2013.01); *C07D 403/10* (2013.01); *C07D 403/12* (2013.01); *C07D 487/10* (2013.01); *C09K 11/07* (2013.01); *H01L 51/0059* (2013.01); *H01L 51/0062* (2013.01)

(58) Field of Classification Search
CPC .................................................... C07D 471/04
See application file for complete search history.

(56) References Cited

U.S. PATENT DOCUMENTS

2016/0164002 A1* 6/2016 Parham ................ C07D 471/04
                                                                          438/47

FOREIGN PATENT DOCUMENTS

KR     2014076522     * 6/2014 .......... C07D 471/04

\* cited by examiner

*Primary Examiner* — Paul V Ward
(74) *Attorney, Agent, or Firm* — WPAT, PC

(57) ABSTRACT

The present invention relates to compounds of the formula (1), to the use thereof in electroluminescent devices, and particularly organic electroluminescence devices, comprising said compounds according to the invention.

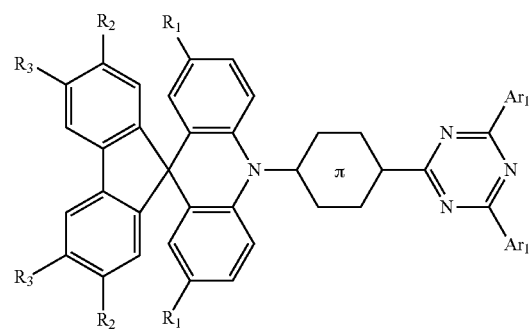

22 Claims, 11 Drawing Sheets

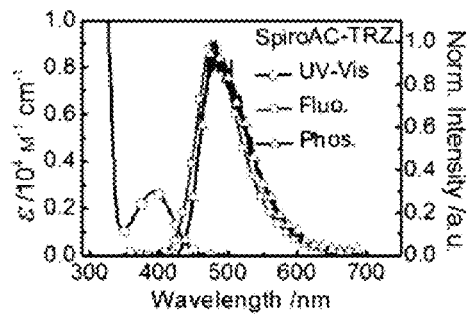 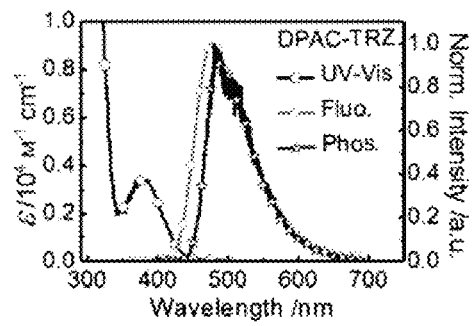
FIG. 2A        FIG. 2B
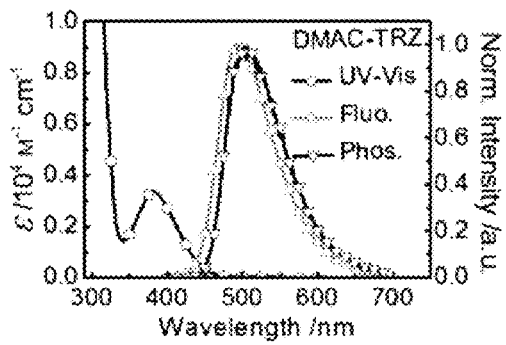
FIG. 2C

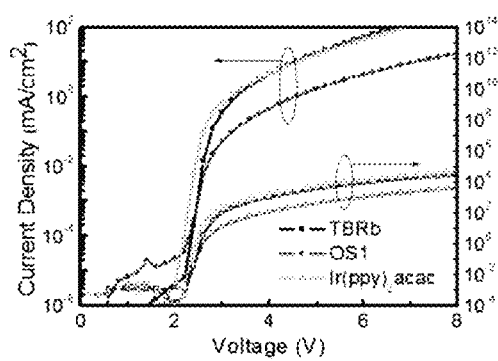
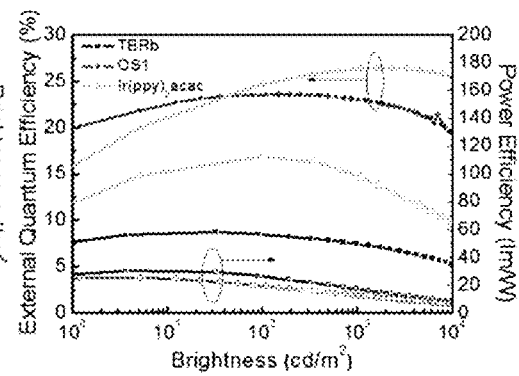
FIG. 6A        FIG. 6B
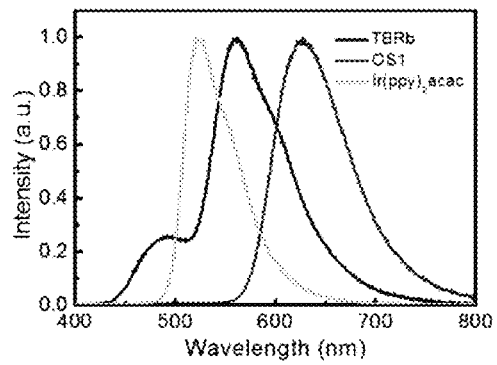
FIG. 6C

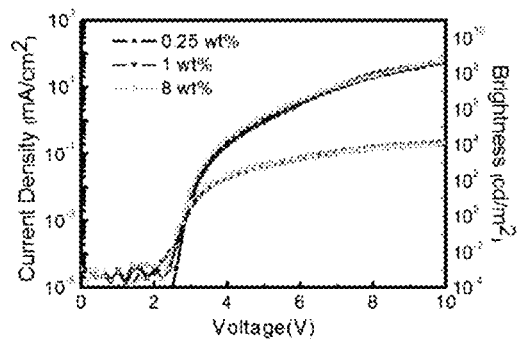
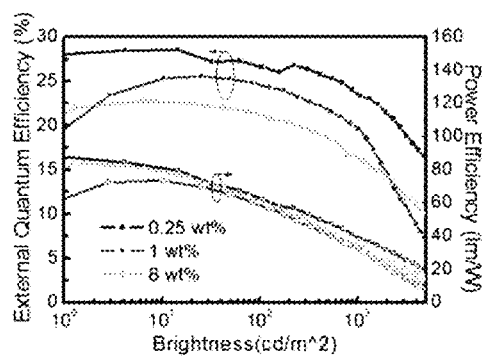
FIG. 7A  FIG. 7B
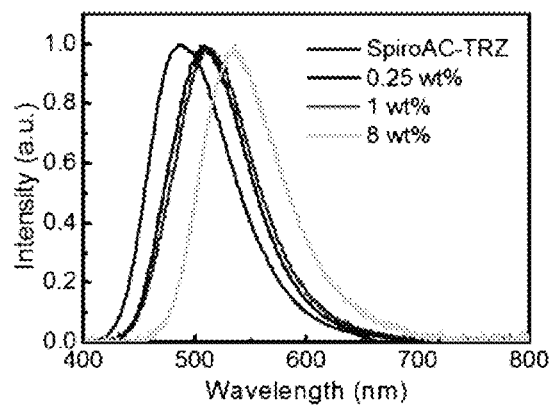
FIG. 7C

SPIROACRIDINE-TRIAZINE HYBRIDS AND APPLICATIONS FOR ELECTROLUMINESCENT DEVICES

CROSS REFERENCE TO RELATED APPLICATIONS

This application claims priority to and the benefit of U.S. Provisional Patent Application Ser. No. 62/391,663, filed on May 9, 2016, the disclosure of which is incorporated by reference in its entirety.

BACKGROUND OF THE INVENTION

1. Field of the Invention

The present invention relates to novel compounds for electroluminescent devices.

2. Description of the Prior Art

The advancement in display and lighting applications of organic light-emitting diodes (OLEDs) has imposed increasing efficiency requirements on OLEDs. To achieve the ideal 100% internal quantum efficiency (IQE), OLED emitters capable of harvesting both singlet and triplet excitons for electroluminescence (EL) have been the subject of extensive researches. The significant advancement was first made through the utilization of precious transition metal-based phosphors. Yet, due to the general rarity and cost considerations of phosphorescent transition metal complexes, metal-free luminophores showing efficient thermally activated delayed fluorescence (TADF) are also emerging as attractive alternatives.

In TADF emitters, by controlling the spatial overlap between the highest occupied molecular orbital (HOMO) and the lowest unoccupied molecular orbital (LUMO), the energy gap ($\Delta E_{ST}$) between the lowest singlet and triplet states can be effectively reduced, rendering efficient reverse intersystem crossing (RISC) for harvesting triplet excitons to generate significant delayed fluorescence. Therefore, in principle, OLED with 100% IQE is achievable using TADF emitters with unitary (100%) photoluminescence.

On the other hand, it is also necessary to raise the optical out-coupling/extraction efficiency of OLEDs to improve the overall external quantum efficiency (EQE) for practical use. In addition to other optical approaches and structures, recent reports have revealed the importance of having emitting dipoles in OLED emitting layers preferentially along the in-plane (horizontal) orientation for optical out-coupling. Since vertical emitting dipoles in OLEDs generally contribute little to external emission and the radiation pattern of horizontal emitting dipoles is more suitable for optical out-coupling, OLED emitters/emitting layers showing an as high as possible horizontal dipole ratio ($\Theta_{//}$, the percentage of horizontal dipoles among all emitting dipoles) are highly desired.

In summary, current requirements for ideal OLED emitters reside not only in high IQE but also in high $\Theta_{//}$ for high EQE. Thus by far, molecular architectures for TADF emitters that can simultaneously provide high photoluminescence quantum yields (PLQYs, $\phi_{PL}$), high OLED IQEs, and high horizontal dipole ratios $\Theta_{//}$ for higher OLED EQEs are yet to be developed and reported.

SUMMARY OF THE INVENTION

In order to overcome the drawbacks of prior arts, the present invention provides various embodiments described below.

In a first embodiment, an spiroacridine-triazine hybrid having the structure of formula (I) is described below:

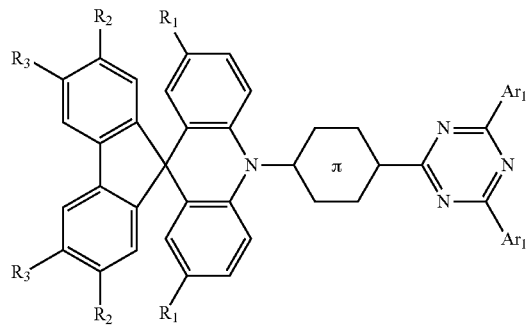

wherein $Ar_1$ is selected from the group consisting of aryl, heteroaryl, multiple fused aryl ring, multiple fused aryl ring with hetero atom(s);

$R_1$, $R_2$, $R_3$ are independently selected from the group consisting of hydrogen atom, linear alkyl, branched alkyl, cyclic alkyl, aryl, heteroaryl, multiple fused aryl ring, multiple fused aryl ring with hetero atom(s); and

is selected from the group consisting of aryl, heteroaryl, multiple fused aryl ring, multiple fused aryl ring with hetero atom(s).

In a second embodiment, an electroluminescent device is disclosed, the electroluminescent device comprises:
 a first electrode;
 a second electrode opposite to the first electrode; and
 one or more organic material layers, which are interposed between the first electrode and the second electrode, and the organic material layers include a light emitting layer;
 wherein at least one of the organic material layers comprises the spiroacridine-triazine hybrid as described in first embodiment.

In one aspect, the present invention provides new molecular architecture based on the spiroacridine-triazine hybrid that can yield a highly efficient TADF emitter simultaneously having high PLQY, excellent thermal stability, and strongly horizontally oriented emitting dipoles. Such a TADF emitter can be used to generate extremely efficient EL with IQE of nearly 100% and EQE of nearly 37% in conventional planar OLED structures (without using any internal/external optical out-coupling schemes). Even higher EQE of >62% can be obtained by adopting the optical out-coupling scheme in the electroluminescent device structure.

The above description is only an outline of the technical schemes of the present invention. Preferred embodiments of the present invention are provided below in conjunction with the attached drawings to enable one with ordinary skill in the art to better understand said and other objectives, features and advantages of the present invention and to make the present invention accordingly.

BRIEF DESCRIPTION OF THE DRAWINGS

The present invention can be more fully understood by reading the following detailed description of the preferred embodiments, with reference made to the accompanying drawings, wherein:

FIG. 2A-2F show electronic absorption spectra and molar extinction coefficient ε (in $CH_2Cl_2$), fluorescence spectra (12 wt. % doped in the mCPCN host, 300 K), and phosphorescence spectra (also in the mCPCN host, 77 K) for (FIG. 2A) SpiroAC-TRZ, (FIG. 2B) DPAC-TRZ, and (FIG. 2C) DMAC-TRZ. (FIG. 2D) PL decay curves of the three compounds doped in the mCPCN host measured at room temperature. (FIG. 2E) PL spectra and (FIG. 2F) PLQYs of SpiroAC-TRZ as a function of the doping concentration in the mCPCN host.

(FIG. 6A) I-V-L characteristics, (FIG. 6B) EQEs, and (FIG. 6C) EL spectra for OLEDs using the emitting layer containing the fluorescent dopant TBRb, the phosphorescent dopant $Os(bpftz)_2(PPhMe_2)_2$(OS1), or the phosphorescent dopant $Ir(ppy)_2acac$ in the SpiroAC-TRZ host.

(FIG. 7A) I-V-L characteristics, (FIG. 7B) EQEs, and (FIG. 7C) EL spectra for OLEDs using the emitting layer comprising the TADF emitter DMACPy56CN (with a concentration of 0.25, 1, and 8 wt %) as the emitting dopant, the SpiroAC-TRZ (12 wt %) as the sensitizer/assistant dopant/co-host in the mCPCN host.

DETAILED DESCRIPTION OF THE PREFERRED EMBODIMENTS

Figure 1:
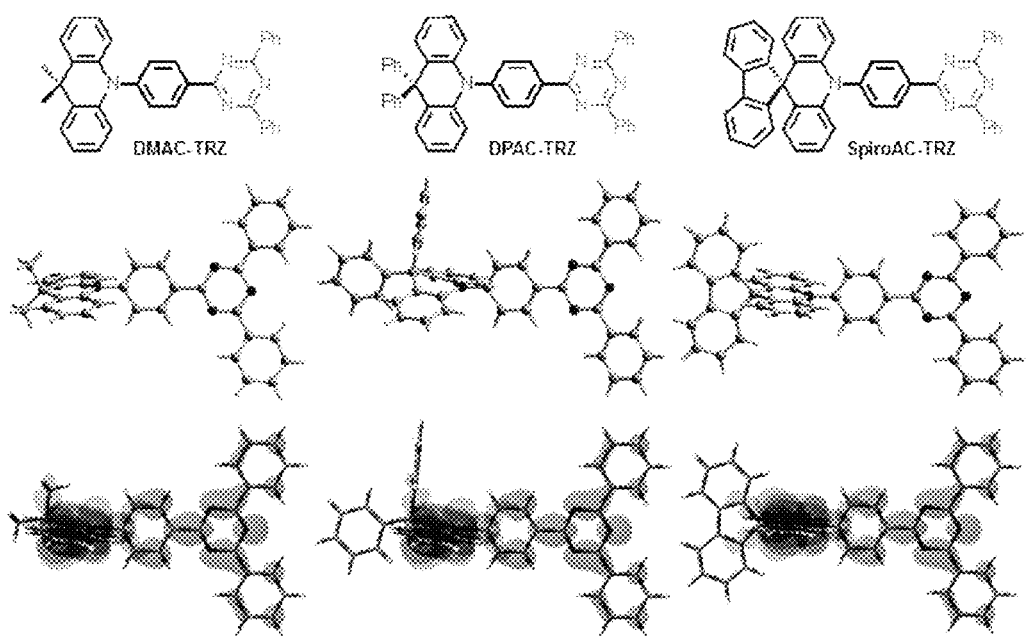
FIG. 1 shows chemical structures [first row], X-ray structures [second row], and calculated HOMO's (blue)/LUMO's (red) [third row] for DMAC-TRZ, DPAC-TRZ, and SpiroAC-TRZ.

In the application, where an element or component is said to be included in and/or selected from a list of recited elements or components, it should be understood that the element or component can be one or more of the recited elements or components, or can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "contain", "contains", "containing", "include," "includes", "including," "have," "has," or "having" should be generally understood as open-ended and non-limiting unless specifically stated otherwise.

Throughout the specification, structures may or may not be presented with chemical names. Where any question arises as to nomenclature, the structure prevails.

In a first embodiment of the present invention, an spiroacridine-triazine hybrid having the structure of formula (I) is described below:

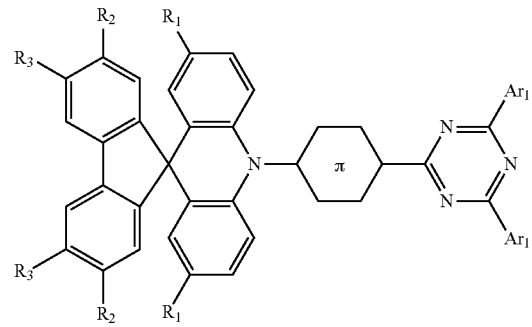

wherein $Ar_1$ is selected from the group consisting of aryl, heteroaryl, multiple fused aryl ring, multiple fused aryl ring with hetero atom(s);

$R_1$, $R_2$, $R_3$ are independently selected from the group consisting of hydrogen atom, linear alkyl, branched alkyl, cyclic alkyl, aryl, heteroaryl, multiple fused aryl ring, multiple fused aryl ring with hetero atom(s); and

is selected from the group consisting of aryl, heteroaryl, multiple fused aryl ring, multiple fused aryl ring with hetero atom(s).

In one example of this embodiment, Ar$_1$ is phenyl.

In another example of this embodiment, R$_1$, R$_2$, R$_3$ are hydrogen atom.

In still another example of this embodiment,

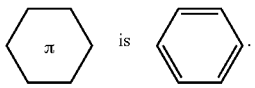

In still another example of this embodiment, the spiroacridine-triazine hybrid has the structure of formula (II) as described below:

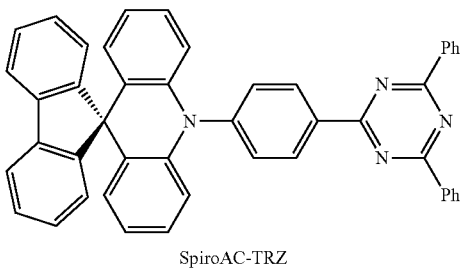

SpiroAC-TRZ

In a second embodiment of the present invention, an electroluminescent device is disclosed, the electroluminescent device comprises:
  a first electrode;
  a second electrode opposite to the first electrode; and
  one or more organic material layers, which are interposed between the first electrode and the second electrode, and the organic material layers include a light emitting layer;
    wherein at least one of the organic material layers comprises the spiroacridine-triazine hybrid as described in the first embodiment.
    wherein the organic material layers further include one or more layer selected from the group consisting of a hole-transporting layer, a hole-blocking layer, an electrode-blocking layer, an electron-transporting layer, and an electron-injecting layer.

In a first example of this embodiment, the emitting layer comprises the spiroacridine-triazine hybrid.

In a second example of this embodiment, the emitting layer is a pure layer composed of the spiroacridine-triazine hybrid.

In a third example of this embodiment, the emitting layer comprises:
  a phosphorescent dopant, a fluorescent dopant, or a thermally activated delayed fluorescent dopant; and
  the spiroacridine-triazine hybrid as an emitting or non-emitting host material.

In a fourth example of this embodiment, the emitting layer comprises:
  a host;
  the spiroacridine-triazine hybrid as a co-host material or an assisted dopant material or an sensitizer material; and
  a fluorescent dopant or a phosphorescent dopant or a thermally activated delayed fluorescent dopant.

In a fifth example of this embodiment, the emitting layer comprises:
  a host material; and
  the spiroacridine-triazine hybrid as an emitting dopant.

In a sixth example of this embodiment, the emitting layer comprises:
  a host material;
  the spiroacridine-triazine hybrid as an emitting dopant; and
  a fluorescent dopant or a phosphorescent dopant or a thermally activated fluorescent dopant as the emitting co-dopant.

In the fourth, fifth, and sixth example, the preferred host material is mCPCN.

In this example, spiroacridine-triazine hybrid is used as an emitting dopant, mCPCN is used as a host material, and the fluorescent dopant or the phosphorescent dopant or the thermally activated fluorescent dopant is yellow or orange-red or red emitting dopant. Therefore, the electroluminescent device could be designed as a hybrid white organic light-emitting diode (WOLED).

In a seventh example of this embodiment, the electroluminescent device further comprises a substrate or superstrate adjacent to the first electrode, and the substrate or superstrate has an outer surface and an inner surface, the inner surface is facing the light emitting layer, and the outer surface is opposite to the inner surface and facing the air.

Wherein the outer surface of the substrate or superstrate is shaped or roughening treated for optical out-coupling, forming regular or irregular patterns, comprising prism, pyramid, macrolens, microlens, micro-prism, micro-pyramid, or grating sheet.

In an eighth example of this embodiment, the electroluminescent device further comprises an optical element adjacent to the outer surface of the substrate or superstrate, and the optical element comprises a prism, a pyramid, a hemisphere lens, a macrolens sheet, a microlens sheet, a micro-prism sheet, a micro-pyramid sheet, a micro-particle layer, a nano-particle layer, a microporous layer, a nanoporous layer, a grating sheet, a scattering sheet, or a diffuser sheet.

The following examples are provided to illustrate further and to facilitate the understanding of the present teachings and are not in any way intended to limit the invention.

Example 1

FIG. 1 depicts one possible molecule embodiment of this invention, SpiroAC-TRZ which has rigid 2,2'-biphenyl (spirobiphenyl) on C(9) of acridine, compared with known compounds DMAC-TRZ and DPAC-TRZ which have alkyl (methyl) and phenyl substitutions on C(9) of acridine, respectively. DPAC-TRZ and SpiroAC-TRZ were obtained in good yields by standard Pd-catalyzed Buchwald-Hartwig amination reaction between the bromotriazine derivative and the designated acridine donor units, and were well characterized by satisfactory spectroscopic analyses. Obtained with the density functional theory (DFT) calculation, FIG. 1 also shows HOMO and LUMO orbitals of the three compounds on optimized geometries. The calculation predicts a significantly twisted configuration (with a large dihedral angle of ~90°) between the acridine and the central phenylene ring bridge for all three compounds, which breaks conjugation between donor/acceptor moieties and causes localization of HOMO and LUMO mainly on the acridine and triphenyltriazine, respectively. As depicted in FIG. 1, single crystal X-ray diffraction (XRD) studies unambiguously confirms their highly twisted molecular structure with a >80° twist angle. Intriguingly, XRD results in FIG. 1 also reveal the significant effect of the C(9) substitution on the conformation of the acridine ring; the rigid spirobiphenyl substitution leads to a nearly planar acridine conformation, while diphenyl and dimethyl substitutions cause a bending along the C(9)-N(10) axis of acridine by an angle of 28° and 110°, respectively.

Figure 2D:
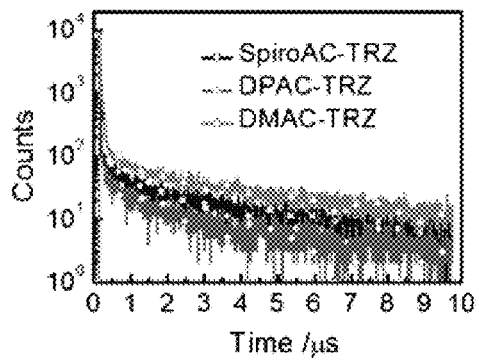
Figure 2E:
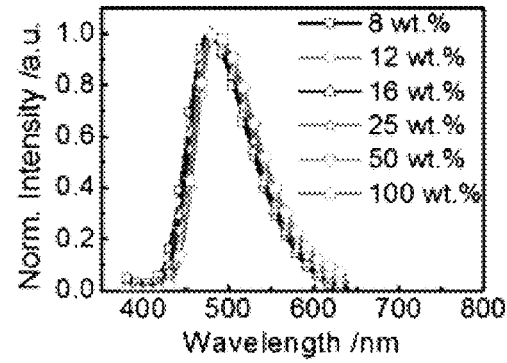
Figure 2F:
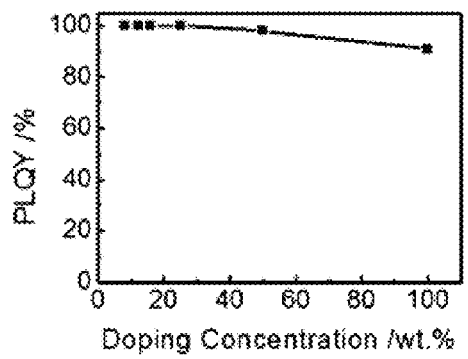

Absorption spectra in solution (CH$_2$Cl$_2$), doped-film fluorescence spectra (12 wt. % doped in the mCPCN host, 300 K), and doped-film phosphorescence spectra (also in the mCPCN host, 77 K) for the three compounds are shown in FIG. 2A-2C, where mCPCN [9-(3-(9H-carbazol-9-yl)phenyl)-9H-carbazole-3-carbonitrile] is a large-triplet-energy bipolar host. Pertinent photophysical data are also listed in Table 1. All three compounds reveal a weak lowest-energy absorption band around 350-450 nm (with the molar extinction coefficient on the order of ~3×10$^3$ M$^{-1}$ cm$^{-1}$), which can be attributed to the intramolecular charge-transfer (ICT) transition from the acridine moiety to the triazine moiety. The fluorescence (phosphorescence) of SpiroAC-TRZ, DPAC-TRZ, and DMAC-TRZ in films give structureless spectra centering around 480 nm (483 nm), 478 nm (482 nm), and 495 nm (504 nm), respectively (Table 1). Compared to the reference compound DMAC-TRZ, both diphenyl and spirobiphenyl substitutions lead to a blue-shifted emission in a same host or solvent (FIG. 2A-2F, Table 1). This may be due to the generally stronger electron-withdrawing capability of the aryl substitution, which could inductively reduce the electron-donating capability of the acridine donor and a blue-shift in emission, as supported by the electrochemical results described below. From the difference in the onset wavelengths of fluorescence and phosphorescence spectra, relatively small $\Delta E_{ST}$ of ~72 meV, 133 meV, and 62 meV are extracted for SpiroAC-TRZ, DPAC-TRZ, and DMAC-TRZ, respectively (Table 1). The transient PL profiles (FIG. 2D) of SpiroAC-TRZ, DPAC-TRZ, and DMAC-TRZ in the mCPCN host measured at 300 K all consist of a fast component (with a lifetime of 17 ns, 15 ns, and 20 ns, respectively, Table 1) and a slow component (with a lifetime of 2.1 μs, 2.9 μs, and 1.9 μs, respectively). The fast and slow decay components can be ascribed to the prompt fluorescence and TADF, respectively. At room temperature, SpiroAC-TRZ, DPAC-TRZ, and DMAC-TRZ in the mCPCN host exhibit a PLQY ($\phi_{PL}$) of 100%, 82%, and 90%, respectively (Table 1). From $\phi_{PL}$ and the contribution ratios of the prompt and delayed components in the transient PL, the quantum yields for the prompt and delayed fluorescence ($\phi_{PF}$ and $\phi_{DF}$, respectively) are obtained and are listed in Table 1 for the three compounds (12 wt. % doped in mCPCN). Noticeably, replacing the dimethyl substitution of the acridine moiety with bulky, rigid and sterical spirobiphenyl substitution (i.e., SpiroAC-TRZ) raises the PLQY to ideal 100%, while the diphenyl substitution leads to noticeable drop of PLQY. Such PLQY results (SpiroAC-TRZ>DMAC-TRZ>DPAC-TRZ) appear to correlate with corformation/bending angles of the acridine moiety detected in XRD studies (SpiroAC-TRZ<DMAC-TRZ<DPAC-TRZ), with the most planar one showing highest PLQY and the most bending one showing lowest PLQY. Highest PLQY of SpiroAC-TRZ is presumably associated with the restriction of torsional/vibrational freedom (and corresponding quenching/deactivation channels) offered by rigid sprioacridine donor. On the other hand, such motions are not restricted for the diphenyl/dimethyl substitution and could even induce bending/motion of the acridine itself. Such results reveal the significant role of the peripheral substitution in emission performances of D-A-type TADF emitters and the distinct benefit of the bulky, rigid and sterical substitution reported here. Intriguingly, SpiroAC-TRZ hardly shows concentration quenching of PL in the solid state. It exhibits a similar PL spectrum and a similarly high PLQY of 100-91% in increasing the concentration from 8 to 100 wt. % (i.e. pure SpiroAC-TRZ film), as shown in the FIG. 2E-2F.

The 2,2'-biphenyl (spirobiphenyl) on C(9) of acridine significantly enhances thermal and morphological stabilities, as characterized by thermogravimetric analysis (TGA) and differential scanning calorimetry (DSC). SpiroAC-TRZ exhibits high decomposition temperatures ($T_d$, corresponding to 5% weight loss) of 353° C., relative to 334° C. of DMAC-TRZ. Meanwhile, significantly higher glass transition temperatures of 155° C. and 136° C. (vs. 90° C. of DMAC-TRZ and 136° C. for DPAC-TRZ) are observed for SpiroAC-TRZ. Cyclic voltammetry of SpiroAC-TRZ reveals both quasi-reversible oxidation and reduction and indicates their promising bipolar electrochemical characteristics. Oxidation/reduction potentials of all three compounds and HOMO/LUMO levels derived therein are summarized in Table 1. The introduction of diaryl substitution leads to slightly higher oxidation potentials and thus slightly deeper HOMO levels (while keeping reduction potentials and LUMO levels more or less intact), enlarging the energy gap. This result clearly indicates the weaker electron-donating behaviour of diaryl-substituted acridine as compared to that of dimethyl-substituted counterpart.

Figure 3A:
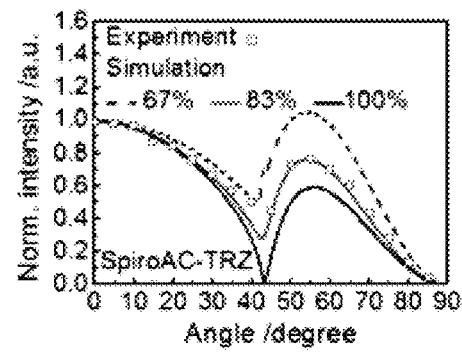
FIG. 3A-3C show measured (symbols) p-polarized PL intensity (at PL peak wavelength) of different emitting layers as a function of the emission angle: for mCPCN:12 wt. % SpiroAC-TRZ, mCPCN:12 wt. % DPAC-TRZ, and mCPCN:12 wt. % DMAC-TRZ. The measured curves are compared to simulated curves (lines) with different horizontal dipole ratios $Θ_{//}$ (e.g., $Θ_{//}$=100% for fully horizontal dipoles and $Θ_{//}$=67% for the isotropic dipole orientation) to extract the horizontal emitting dipole ratios of different emitting layers.
Figure 3B:
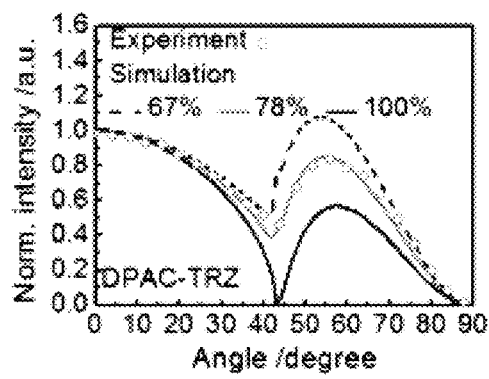
Figure 3C:
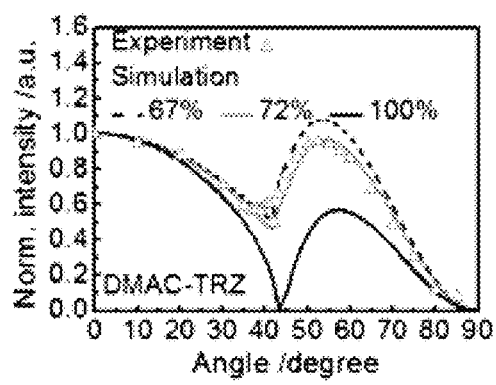
Figure 3D:
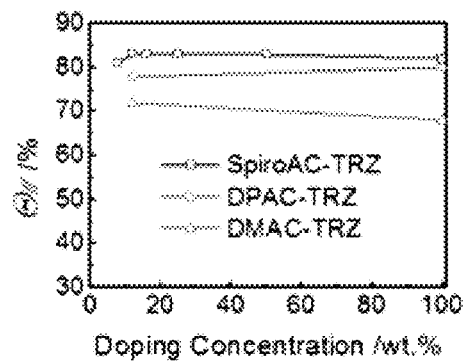
FIG. 3D shows horizontal dipole ratios $Θ_{//}$ of the three compounds as a function of the doping concentration.
Figure 3E:
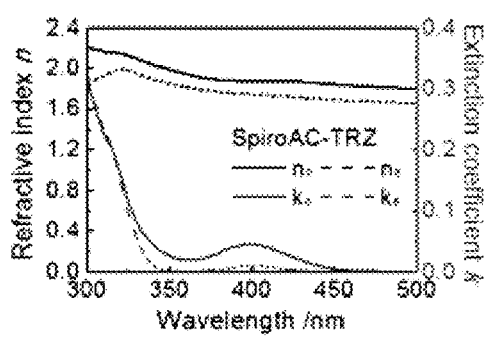
FIG. 3E-3G show ordinary (in-plane) and extraordinary (out-of-plane) refractive indices ($n_o$, $n_e$) and extinction coefficients ($k_o$, $k_e$) of pure (non-doped) films of the three compounds.
Figure 3F:
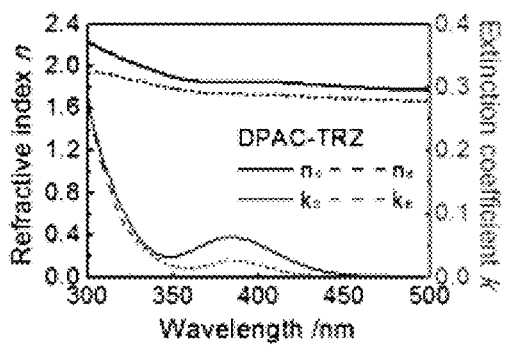
Figure 3G:
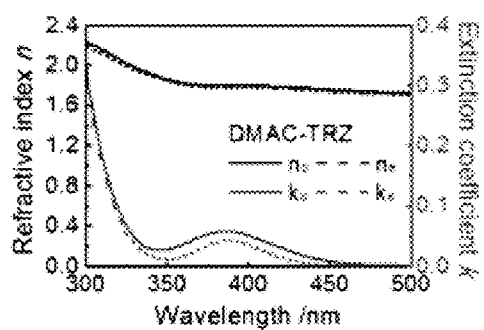
Figure 3H:
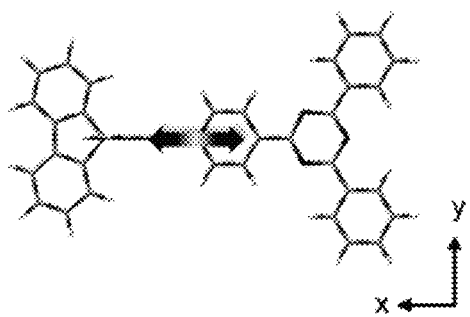
FIG. 3H shows the direction of the calculated $S_0$-$S_1$ transition dipole moment (as indicated by the colored arrow) of SpiroAC-TRZ relative to the coordinate of the molecular structure.

Emitting dipole orientations of these compounds (12 wt. % in the mCPCN host) were characterized by the angle- and polarization-resolved photoluminescence. Measured p-polarized PL intensities (at the PL peak wavelength) as a function of the emission angle for three compounds in mCPCN are shown in FIG. 3A-3C. The measured curves are compared to simulated curves with different horizontal dipole ratios $\Theta_{//}$ (e.g., $\Theta_{//}$=100% for fully horizontal dipoles and $\Theta_{//}$=67% for the isotropic dipole orientation) to extract $\Theta_{//}$'s of different compounds in emitting layers. $\Theta_{//}$'s thus determined for SpiroAC-TRZ, DPAC-TRZ, and DMAC-TRZ (Table 1) are 83%, 78%, and 72%, respectively. SpiroAC-TRZ having the bulky, rigid, sterical and planar spirobiphenyl substitution exhibits a strongest tendency of orienting emitting dipoles horizontally in a same mCPCN host. FIG. 3D further depicts the horizontal dipole ratios $\Theta_{//}$ of the three compounds as a function of the doping concentration, including the cases of non-doped (pure) films (i.e., 100%). They hardly show dependence on the doping concentration, suggesting that in these cases the tendency of preferential dipole orientation is more a natural characteristic of compounds themselves and is not strongly perturbed/affected by the host. To further elucidate mechanisms of molecular and dipole orientations, spectroscopic ellipsometry was conducted on non-doped (pure) films of the three compounds. FIG. 3E-3G depict the ordinary (in-plane) and extraordinary (out-of-plane) refractive indices ($n_o$, $n_e$) and extinction coefficients ($k_o$, $k_e$) of pure (non-doped) films of the three compounds, which clearly indicate strongest anisotropic optical properties and largest difference between in-plane and out-of-plane ICT absorption (350-450 nm) for SpiroAC-TRZ (than for DPAC-TRZ and DMAC-TRZ). Quantum chemical calculation reveals that the $S_0$-$S_1$ transition dipole moment of the acridine-triazine hybrid is mainly along the long axis of the molecular structure (FIG. 3H). Such results thus suggest that these compounds have a natural tendency to align their molecular long axes horizontally upon anchoring onto a surface. That SpiroAC-TRZ exhibits the strongest anisotropy and highest horizontal dipole ratio $\Theta_{//}$ is perhaps due to its overall more planar and balanced/symmetrical structure compared to the other two compounds, since spirobiphenyl and triphenyltriazine on two sides of acridine are nearly co-planar (FIG. 1). In addition, the highest $T_g$ of SpiroAC-TRZ may also help to suppress surface mobility/orientational rearrangement during film deposition and have molecular/dipole orientations frozen.

In summary, molecules based on the spiroacridine-triazine hybrid can yield a highly efficient emitter simultaneously possessing high PLQY, excellent thermal stability, strongly horizontally oriented emitting dipoles, and low concentration quenching.

TABLE 1

The summary of physical and photophysical properties of DMAC-TRZ, DPAC-TRZ, and SpiroAC-TRZ.

|  | SpiroAC-TRZ | DPAC-TRZ | DMAC-TRZ |
| --- | --- | --- | --- |
| $\lambda_{max,fl}$ [nm][a] | 480 | 478 | 495 |
| $\lambda_{max,ph}$ [nm][a] | 483 | 482 | 504 |
| $\Delta E_{ST}$ [meV][a] | 72 | 133 | 62 |
| $\Phi_{PL}$ [%][a] | 100 | 82 | 90 |
| $\Phi_{PF}$ [%][a] | 79 | 70 | 59 |
| $\Phi_{DF}$ [%][a] | 21 | 12 | 31 |
| $\tau_{PF}$ [ns][a] | 17 | 15 | 20 |
| $\tau_{DF}$ [µs][a] | 2.1 | 2.9 | 1.9 |
| $\Theta_{//}$ [%][a] | 83 | 78 | 72 |
| Td [° C.][b] | 353 | 368 | 334 |
| Tg [° C.][c] | 155 | 136 | 90 |
| $E_{1/2}^{ox}$ [V][d] | 1.06 | 1.08 | 0.97 |
| $E_{1/2}^{red}$ [V][d] | −1.49 | −1.49 | −1.46 |
| HOMO [eV][e] | 5.70 | 5.72 | 5.61 |
| LUMO [eV][f] | 3.12 | 3.12 | 3.12 |

[a]fluorescence maximum wavelength, phosphorescence maximum wavelength, energy gap between lowest singlet and triplet states, photoluminescence quantum yield, the quantum yield for the prompt fluorescence, the quantum yield for the delayed fluorescence, lifetime of the prompt component in transient PL, lifetime of the delayed component in transient PL, and horizontal dipole ratio measured in doped mCPCN films (with 12 wt. % doping concentration);
[b]decomposition temperature corresponding to 5% weight loss in the thermogravimetric analyses;
[c]glass transition temperature;
[d]oxidation and reduction half-wave potentials in cyclic voltammetry;
[e]HOMO level calculated from the oxidation half-wave potential;
[f]LUMO level estimated from the reduction onset potential.

Example 2

The spiroacridine-triazine hybrid can be applied for EL devices. One possible device embodiment architecture used it as the emitting dopant (mixed with a host material) in the emitting layer: glass substrate/ITO/MoO₃ (1 nm)/TAPC (50 nm)/mCP (10 nm)/mCPCN doped with the emitting dopant (12 wt. %, 20 nm)/3TPYMB (50 nm)/LiF (0.5 nm)/Al (150 nm). Indium tin oxide (ITO) and Al were anode and cathode, respectively. Di-[4-(N,N-ditolyl-amino)-phenyl]-cyclohexane (TAPC) and N,N-dicarbazolyl-3,5-benzene (mCP) were hole-transport layers (HTL). The bipolar mCPCN host constituted the emitting layer (EML). Tris-[3-(3-pyridyl)mesityl]borane (3TPYMB) was the electron-transport layer (ETL). [4,9,20] MoO₃ and LiF were employed as hole and electron-injection layers.

Figure 4A:
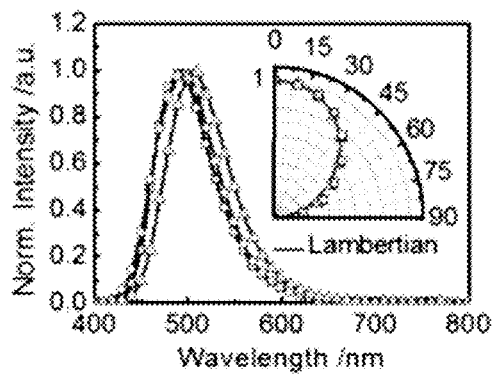
FIG. 4A-4D show EL spectra (measured without attaching extraction lens), I-V-L characteristics (measured without attaching extraction lens), EQEs (measured without or with attaching extraction lens), and luminous efficiencies (measured without or with attaching extraction lens) for SpiroAC-TRZ, DPAC-TRZ, DMAC-TRZ devices with the doping concentration of 12 wt. %. The inset of FIG. 4A depicts the EL emission patterns of the three devices, along with the Lambertian distribution.
Figure 4B:
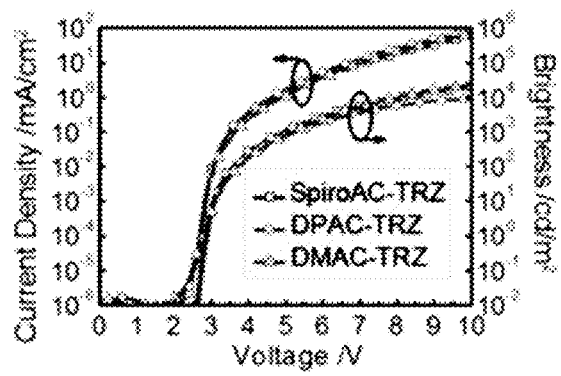
Figure 4C:
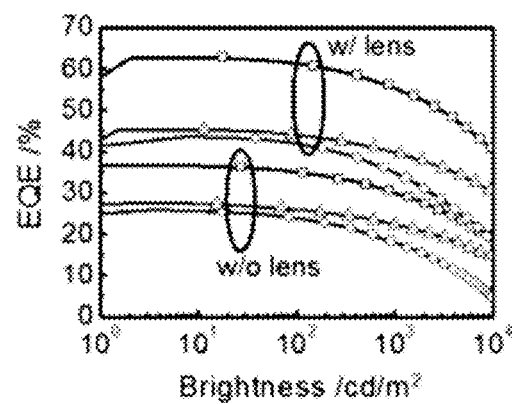
Figure 4D:
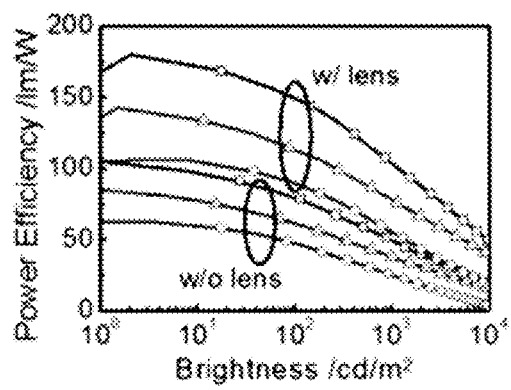
Figure 4E:
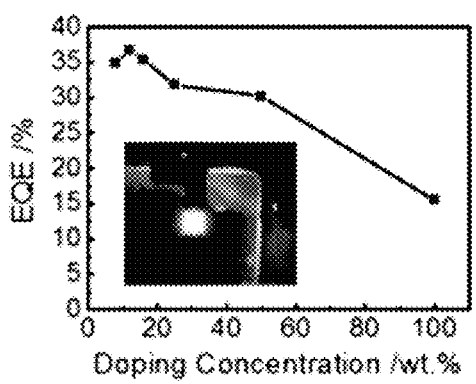
FIG. 4E shows EQEs of SpiroAC-TRZ devices as a function of the doping concentration. The inset of FIG. 4E shows the photo of a SpiroAC-TRZ device (12 wt. %).

Representative EL characteristics of OLEDs using SpiroAC-TRZ as the emitting dopant (with doping concentration of 12 wt. %), compared with DPAC-TRZ and DMAC-TRZ, are shown in FIG. 4A-4D, while performance parameters of all devices are summarized in Table 2. The EL spectrum of SpiroAC-TRZ represents sky blue EL and is similar to corresponding PL spectrum in doped films. EL emission patterns are generally lambertian (inset of FIG. 4A). These SpiroAC-TRZ device exhibits a rather low turn-on voltage of ~2 V and low operation voltage (e.g., ~3 V for a brightness of 100 cd·m$^{-2}$). Under a same device architecture, the devices based on SpiroAC-TRZ, DPAC-TRZ, and DMAC-TRZ show EL efficiencies of up to (36.7%, 94 cd·A$^{-1}$, 98.4 lm·W$^{-1}$), (25.8%, 60 cd·A$^{-1}$, 62.7 lm·W$^{-1}$), and (27.4%, 77.1 cd·A$^{-1}$, 80.8 lm·W$^{-1}$), respectively. These EQEs correspond rather quantitatively with the PLQYs and horizontal dipole ratios $\Theta_{//}$'s of these compounds (see Table 2). Most importantly, the compound SpiroAC-TRZ having highest PLQY and $\Theta_{//}$ gives the highest EQE of ~37% among the three compounds. Even more intriguingly, such a high EQE is obtained in the (sky) blue TADF OLED (see inset of FIG. 4E for the photo of the SpiroAC-TRZ device). The SpiroAC-TRZ device exhibits a low efficiency roll-off and retains a high EQE of ~30.5% even at the high brightness of 1000 cd·m$^{-2}$.

Figure 4F:
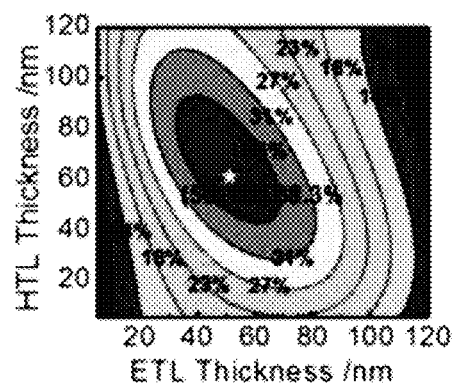
FIG. 4F shows calculated optical out-coupling efficiency for the SpiroAC-TRZ device (12 wt. %) as a function of the HTL and ETL thicknesses.
Figure 5A:
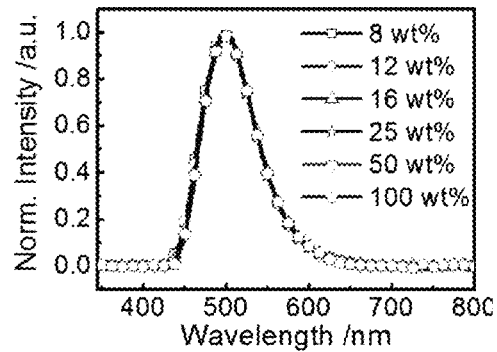
FIG. 5A shows EL spectra (measured without attaching extraction lens)
Figure 5B:
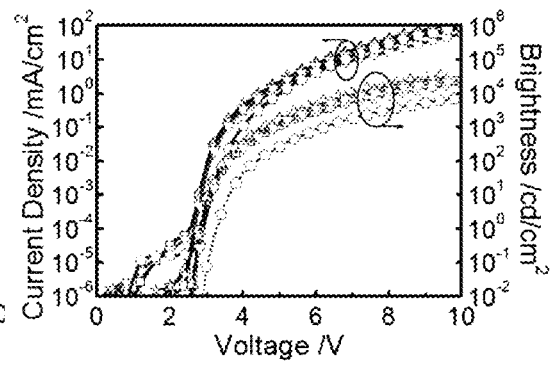
FIG. 5B shows I-V-L characteristics (measured without attaching extraction lens)
Figure 5C:
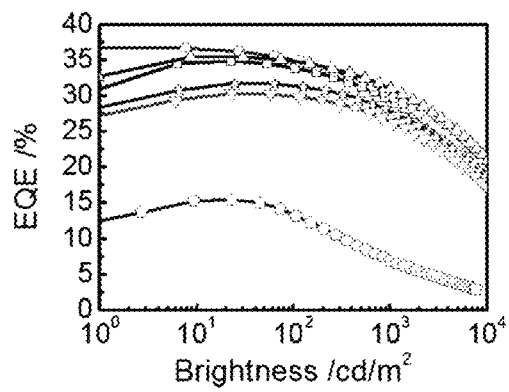
FIG. 5C shows EQEs (measured without attaching extraction lens)
Figure 5D:
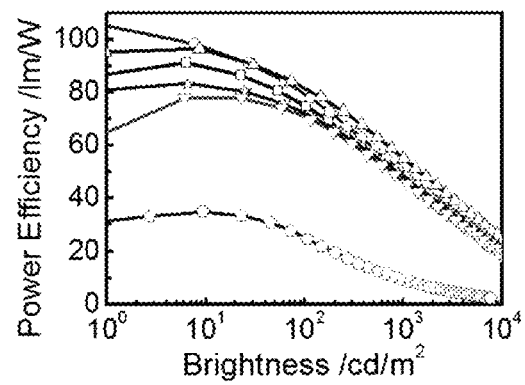
FIG. 5D shows luminous efficiencies (measured without attaching extraction lens) for SpiroAC-TRZ devices having a 8, 12, 16, 25, 50, 100 wt. % doping concentration in the mCPCN host of the emitting layer.

To get more insights of the very high EQE obtained, IQE and optical out-coupling efficiency are further analyzed. Assuming generation ratios of 0.25 and 0.75 for singlet and triplet excitons, respectively, the EQE of TADF OLEDs can generally be expressed as:

$$EQE = IQE \times \phi_{out} = (\gamma \times \eta_{exc}) \times \phi_{out} \quad (1)$$

$$\eta_{exc} = 0.25 \times \phi_{PF} + 0.25 \times \phi_{DF} + 0.75 \times \phi_{RISC} \times \phi_{PL} = \phi_{PL} \times (0.25 + 0.75 \times \phi_{RISC}) \quad (2)$$

where $\gamma$ is the carrier recombination efficiency (for forming excitons), $\eta_{exc}$ is the overall utilization efficiency of electrically generated excitons for (fluorescence) photon emission, $\phi_{out}$ is the optical out-coupling efficiency, and $\phi_{RISC}$ is the efficiency of tiplet-to-singlet reverse intersystem crossing. With $\phi_{RISC} \sim 1$ (i.e., small non-radiative loss in the triplet excited state relative to intersystem crossing) for relatively efficient TADF emitters and $\gamma \sim 1$ as well for efficient devices, the ultimate IQE for TADF OLEDs would be $\phi_{PL}$ and the ultimate EQE would be $\phi_{PL} \times \phi_{out}$. In Table 2, $\phi_{PL}$ and $\phi_{PL} \times \phi_{out}$ are input as the ultimate IQE and EQE and are compared with experimental EQE. $\phi_{out}$ of various OLEDs can be calculated using the classical oscillating dipole model, taking into consideration distributions of dipole orientations (using measured $\Theta_{//}$ as the input), dipole locations (in the emitting layer), and dipole frequencies (using the PL spectra as the input), in the emitting layer. FIG. 4F shows the calculated optical out-coupling efficiencies of internally generated radiation into air for the SpiroAC-TRZ device as a function of the ETL and the HTL thicknesses. Maximal out-coupling efficiencies of ~38.3%, 35.7%, and 33.1% are obtained for SpiroAC-TRZ, DPAC-TRZ, and DMAC-TRZ devices (Table 2), respectively. Such results clearly confirm the benefit of more horizontally oriented emitting dipoles to light extraction of OLEDs. The rather good agreement between calculated $\phi_{PL} \times \phi_{out}$ and experimentally obtained EQEs (Table 2) for SpiroAC-TRZ devices indicates rather ideal $\gamma$ (~1) and small non-radiative loss in the triplet state (thus $\phi_{RISC} \sim 1$), having IQE approach the ultimate $\phi_{PL}$ for each device.

TABLE 2

The summary of OLED characteristics (with 12 wt. % doping in the emitting layer)

| | | $\eta_{ext}$ [%] [a] max., 100, 1000 cd m$^{-2}$ | $\eta_c$ [cd A$^{-1}$] [b] max., 100, 1000 cd m$^{-2}$ | $\eta_p$ [lm W$^{-1}$] [c] max., 100, 1000 cd m$^{-2}$ | $\Phi_{PL}$ [%] | $\Theta_{//}$ [%] | $\Phi_{out}$ [%] [d] | $\Phi_{PL} \times \Phi_{out}$ [%] |
|---|---|---|---|---|---|---|---|---|
| SpiroAC-TRZ | w/o lens | 36.7, 34.9, 30.5 | 94, 89.3, 78.2 | 98.4, 77.9, 51.2 | 100 | 83 | 38.3 | 38.3 |
| | w/lens | 62.8, 60.8, 54.2 | | 168.3, 133.2, 93.6 | | | | |
| DPAC-TRZ | w/o lens | 25.8, 24.1, 18.3 | 60, 56, 42.4 | 62.7, 48.8, 25.6 | 82 | 78 | 35.7 | 29.3 |
| | w/lens | 43.6, 40.8, 32.2 | | 105.9, 89.9, 47 | | | | |
| DMAC-TRZ | w/o lens | 27.4, 25.8, 22.4 | 77.1, 72.5, 63 | 80.8, 60, 38.1 | 90 | 72 | 33.1 | 29.8 |
| | w/lens | 46.6, 43.4, 38.5 | | 133.3, 106.5, 66.8 | | | | |

[a] external quantum efficiency.
[b] current efficiency.
[c] power efficiency.
[d] calculated out-coupling efficiency.

Example 3

With a same device structure, EL devices containing SpiroAC-TRZ can also be implemented with different doping concentrations, ranging from 8 to 100 wt. % (i.e. non-doped SpiroAC-TRZ device). The device EQE as a function of the doping concentration is summarized in FIG. 4E, with detailed EL characteristics of these devices being shown in FIG. 5. It is seen that high EQEs of ~15-37% can be obtained throughout the whole concentration range, including the device using the non-doped/pure SpiroAC-TRZ as the emitting layer.

Example 4

The outer surface of the substrate in embodiment example 2 may be further attached with an extraction lens to further increase EQE of the EL device. When measuring EL characteristics of these devices by attaching a large index-matched hemisphere lens (with a diameter of 1.5 cm) to the substrate surface to effectively extract radiation coupled into the substrate, an even higher EQE of 62.8% was further obtained for the SpiroAC-TRZ device (FIGS. 4A-4F and Table 2), clearly manifesting the great potential for achieving even higher EQEs from such emitters with effective light extraction schemes.

Example 5

For instance, the out-coupling lens attached to the substrate in example 4 may be replaced with other out-coupling optical element adjacent to the outer surface of the substrate, such as a prism, a pyramid, a hemisphere lens, a macrolens sheet, a microlens sheet, a micro-prism sheet, a micro-pyramid sheet, a micro-particle layer, a nano-particle layer, a microporous layer, a nanoporous layer, a grating sheet, a scattering sheet, a diffuser sheet, arrays of pores, arrays of crevices, arrays of air bubbles, arrays of vacuum pores etc.

Example 6

For instance, the out-coupling lens attached to the substrate in example 4 may be replaced with other out-coupling surface treatment, such as shaped or roughening treated, forming regular or irregular patterns, such as prism, pyramid, macrolens, microlens, micro-prism, micro-pyramid, or grating etc.

Example 7

The high performance SpiroAC-TRZ material can also be used in different ways in various OLED device architectures.

(i) One may use it as the host material in OLED emitting layers for the fluorescent emitting dopant, the phosphorescent emitting dopant, or the TADF emitting dopant.

For instance, FIG. 6A-6C show I-V-L characteristics, EQEs, and EL spectra for OLEDs using the emitting layer containing the fluorescent dopant TBRb, the phosphorescent dopant Os(bpftz)$_2$(PPhMe$_2$)$_2$(OS1), or the phosphorescent dopant Ir(ppy)$_2$acac in the SpiroAC-TRZ host. The device structures for these three devices are:

ITO/MoO3 (1 nm)/TAPC (40 nm)/TCTA(10 nm)/SpiroAC-TRZ: TBRb 1 wt % (20 nm)/B3PYMPM (50 nm)/LiF (0.5 nm)/Al (150 nm).

ITO/MoO3 (1 nm)/TAPC(60 nm)/TCTA(10 nm)/SpiroAC-TRZ: OS1 2.5 wt % (20 nm)/B3PYMPM(60 nm)/LiF (0.5 nm)/Al (150 nm)

ITO/MoO3 (1 nm)/TAPC(50 nm)/TCTA(10 nm)/SpiroAC-TRZ: Ir(ppy)2acac 8% (20 nm)/B3PYMPM(50 nm)/LiF (0.5 nm)/Al (150 nm)

In FIG. 6A-6C, very small efficiency roll-offs are observed in all three devices despite using either fluorescent or phosphorescent dopants.

(ii) One may use it as the assisted dopant/sensitizer/co-host in OLED emitting layers for sensitizing the fluorescent emitting dopant, the phosphorescent emitting dopant, or the TADF emitting dopant.

For instance, FIG. 7A-7C show I-V-L characteristics, EQEs, and EL spectra for OLEDs using the emitting layer comprising the TADF emitter DMACPy56CN (with a concentration of 0.25, 1, and 8 wt %) as the emitting dopant, and the SpiroAC-TRZ (12 wt %) as the sensitizer/assistant dopant/co-host in the mCPCN host. The device structures for these devices are:

ITO/MoO3 (1 nm)/TAPC (50 nm)/mCP(10 nm)/SpiroAC-TRZ:DMACPy56CN (0.25 wt. %, 1 wt. %, or 8 wt. %, 20 nm)/3TPYMB (50 nm)/LiF (0.5 nm)/Al (150 nm).

In FIG. 7A-7C, a rather high EQE of ~27% is achieved with such a device structure.

(iii) One may use it as the co-dopant in OLED emitting layers with other fluorescent emitting dopant, phosphorescent emitting dopant, or TADF emitting dopant for white OLEDs or OLEDs giving combination of colors.

Figure 8A:
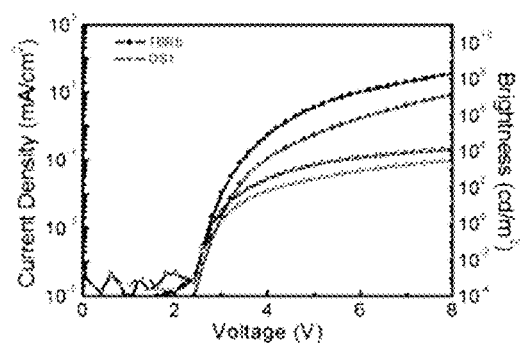
(FIG. 8A) I-V-L characteristics, (FIG. 8B) EQEs, and (FIG. 8C) EL spectra for white OLEDs using the emitting layer containing the fluorescent dopant TBRb or the phosphorescent dopant $Os(bpftz)_2(PPhMe_2)_2$(OS1) co-doped with SpiroAC-TRZ in the mCPCN host.
Figure 8B:
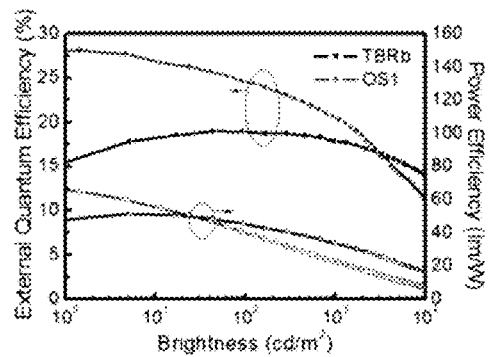
Figure 8C:
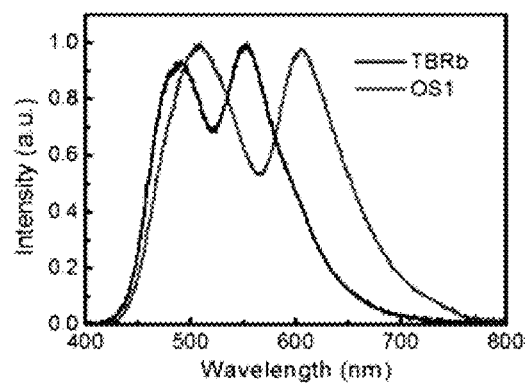

For instance, FIG. 8A-8C show I-V-L characteristics, EQEs, and EL spectra for white OLEDs using the emitting layer containing the fluorescent dopant TBRb or the phosphorescent dopant Os(bpftz)$_2$(PPhMe$_2$)$_2$(OS1) co-doped with SpiroAC-TRZ in the mCPCN host. The device structures for these devices are:

ITO/MoO$_3$ (1 nm)/TAPC (50 nm)/mCP (10 nm)/mCPCN: SpiroAC-TRZ 12 wt %: TBRb 0.5 wt % (20 nm)/3TPYMPB (50 nm)/LiF (0.5 nm)/Al (150 nm)

ITO/MoO$_3$ (1 nm)/TAPC(60 nm)/mCP (10 nm)/mCPCN: SpiroAC-TRZ 12 wt %: OS1 0.25 wt % (20 nm)/3TPYMB (50 nm)/LiF (0.5 nm)/Al (150 nm)

In FIG. 8A-8C, a very high EQE of ~28% is obtained with the WOLED containing the SpiroAC-TRZ and the phosphorescent dopant Os(bpftz)$_2$(PPhMe$_2$)$_2$ co-doped in the emitting layer (mCPCN host). A decently high EQE of ~20% could also be obtained with the WOLED containing the SpiroAC-TRZ and the fluorescent dopant TBRB co-doped in the emitting layer (mCPCN host).

These different example applications of SpiroAC-TRZ indicates its potential for a wide range of applications in OLED technologies.

The above embodiments are only used to illustrate the principles of the present invention, and they should not be construed as to limit the present invention in any way. The above embodiments can be modified by those with ordinary skill in the art without departing from the scope of the present invention as defined in the following appended claims.

What is claimed is:

1. An spiroacridine-triazine hybrid having the structure of formula (I) as described below:

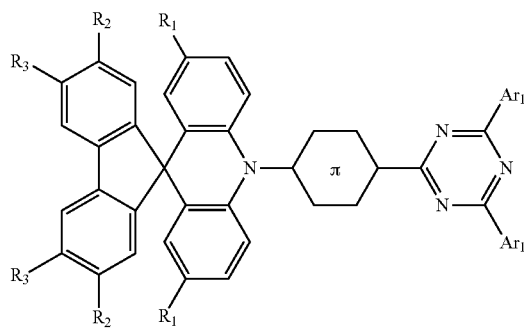

wherein
Ar1 is selected from the group consisting of aryl, heteroaryl, multiple fused aryl ring, multiple fused aryl ring with hetero atom(s);
R1, R2, R3 are independently selected from the group consisting of hydrogen atom, linear alkyl, branched alkyl, cyclic alkyl, aryl, heteroaryl, multiple fused aryl ring, multiple fused aryl ring with hetero atom(s); and

is selected from the group consisting of aryl, heteroaryl, multiple fused aryl ring, multiple fused aryl ring with hetero atom(s).

2. The spiroacridine-triazine hybrid of claim 1, wherein Ar1 is phenyl.

3. The spiroacridine-triazine hybrid of claim 1, wherein R1, R2, R3 are hydrogen atom.

4. The spiroacridine-triazine hybrid of claim 1, wherein

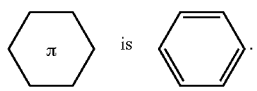 [SMILES: C1CCCCC1 ; c1ccccc1]

5. The spiroacridine-triazine hybrid of claim 1, having the structure of formula (II) as described below:

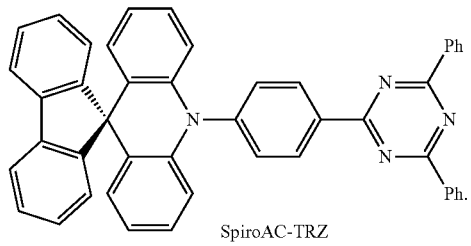

SpiroAC-TRZ

6. An electroluminescent device, comprising:
a first electrode;
a second electrode opposite to the first electrode; and
one or more organic material layers, which are interposed between the first electrode and the second electrode, and the organic material layers include a light emitting layer;
wherein at least one of the organic material layers comprises the spiroacridine-triazine hybrid of claim 1.

7. The electroluminescent device of claim 6, wherein the organic material layers further include one or more layer selected from the group consisting of a hole-transporting layer, a hole-blocking layer, an electrode-blocking layer, an electron-transporting layer, and an electron-injecting layer.

8. The electroluminescent device of claim 6, wherein the emitting layer comprises the spiroacridine-triazine hybrid of claim 1.

9. The electroluminescent device of claim 8, wherein the emitting layer is a pure layer composed of the spiroacridine-triazine hybrid.

10. The electroluminescent device of claim 8, wherein the emitting layer comprises:
a phosphorescent dopant, a fluorescent dopant, or a thermally activated delayed fluorescent dopant; and
the spiroacridine-triazine hybrid as an emitting or non-emitting host material.

11. The electroluminescent device of claim 8, wherein the emitting layer comprises:
a host;
the spiroacridine-triazine hybrid as a co-host material or an assisted dopant material or an sensitizer material; and
a fluorescent dopant or a phosphorescent dopant or a thermally activated delayed fluorescent dopant.

12. The electroluminescent device of any one of claim 11, wherein the host material is mCPCN.

13. The electroluminescent device of claim 8, wherein the emitting layer comprises:
a host material; and
the spiroacridine-triazine hybrid as an emitting dopant.

14. The electroluminescent device of any one of claim 13, wherein the host material is mCPCN.

15. The electroluminescent device of claim 8, wherein the emitting layer comprises:
a host material;
the spiroacridine-triazine hybrid as an emitting dopant; and
a fluorescent dopant or a phosphorescent dopant or a thermally activated fluorescent dopant as the emitting co-dopant.

16. The electroluminescent device of any one of claim 15, wherein the host material is mCPCN.

17. The electroluminescent device of claim 15, wherein the fluorescent dopant or the phosphorescent dopant or the thermally activated fluorescent dopant is yellow or orange-red or red emitting dopant, and the electroluminescent device is a white organic light-emitting diode (WOLED).

18. The electroluminescent device of claim 6, further comprising a substrate or superstrate adjacent to the first electrode, and the substrate or superstrate has an outer surface and an inner surface, the inner surface is facing the light emitting layer, and the outer surface is opposite to the inner surface and facing the air.

19. The electroluminescent device of claim 18, wherein the outer surface of the substrate or superstrate is shaped or roughening treated for optical out-coupling, forming regular or irregular patterns.

20. The electroluminescent device of claim 19, wherein the pattern comprising prism, pyramid, macrolens, microlens, micro-prism, micro-pyramid, or grating sheet.

21. The electroluminescent device of claim 18, further comprising an optical element adjacent to the outer surface of the substrate or superstrate.

22. The electroluminescent device of claim 21, wherein the optical element comprising a prism, a pyramid, a hemisphere lens, a macrolens sheet, a microlens sheet, a micro-prism sheet, a micro-pyramid sheet, a micro-particle layer, a nano-particle layer, a microporous layer, a nanoporous layer, a grating sheet, a scattering sheet, or a diffuser sheet.

* * * * *